United States Patent [19]

Haugwitz

[11] 4,312,809

[45] Jan. 26, 1982

[54] LACTAM DERIVATIVES OF MERCAPTOACYLAMINO ACIDS

[75] Inventor: Rudiger D. Haugwitz, Titusville, N.J.

[73] Assignee: E. R. Squibb & Sons, Inc., Princeton, N.J.

[21] Appl. No.: 202,851

[22] Filed: Oct. 31, 1980

[51] Int. Cl.³ .................... A61K 31/40; C07D 401/12
[52] U.S. Cl. .......................... 260/325 PH; 424/240; 424/246; 424/250; 424/251; 424/274
[58] Field of Search ................................. 260/325 PH

[56] References Cited

U.S. PATENT DOCUMENTS

| | | |
|---|---|---|
| 4,105,776 | 8/1978 | Ondetti et al. |
| 4,154,935 | 5/1979 | Ondetti et al. |
| 4,168,267 | 9/1979 | Petrillo |

FOREIGN PATENT DOCUMENTS

| | | |
|---|---|---|
| 879158 | 10/1959 | Belgium |
| 2027025 | 2/1980 | United Kingdom |
| 2028327 | 3/1980 | United Kingdom |

OTHER PUBLICATIONS

Helv. Chim. Acta, 42, 1085 (1959).

Primary Examiner—Alton D. Rollins
Attorney, Agent, or Firm—Lawrence S. Levinson; Donald J. Barrack

[57] ABSTRACT

Angiotensin converting enzyme inhibitory action is shown in mammals by compounds having the formula

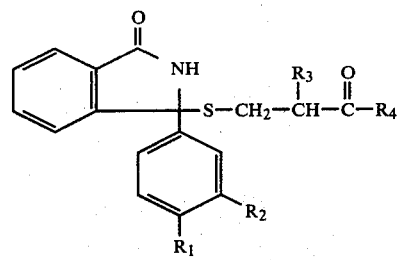

wherein
$R_1$ and $R_2$ are the same or different, and each is hydrogen, halogen, trifluoromethyl, or aminosulfonyl;
$R_3$ is hydrogen, alkyl, halogen or trifluoromethyl;
$R_4$ is proline or a proline derivative;
$R_5$ is hydrogen, alkyl, phenylalkyl, or a metal ion;
$R_6$ is hydrogen, hydroxy, alkyl, halogen, azido, amino, cycloalkyl, aryl, arylalkyl, carbamoyloxy, N,N-dialkylcarbamoyloxy, or $-Y-R_9$;
$R_7$ and $R_7'$ are the same and each is halogen or $-Y-R_{10}$, or $R_7$ and $R_7'$ together are $=O$, $-O-(CH_2)_m-O-$ or $-S-(CH_2)_m-S-$;
$R_8$ is hydrogen and $R_8'$ is phenyl, 2-hydroxyphenyl or 4-hydroxyphenyl or $R_8$ and $R_8'$ together are $=O$;
$R_9$ is alkyl, aryl, arylalkyl, 1- or 2-naphthyl, or biphenyl;
$R_{10}$ is alkyl, aryl or arylalkyl;
Y is oxygen or sulfur; and
m is 1 or 2.

7 Claims, No Drawings

LACTAM DERIVATIVES OF MERCAPTOACYLAMINO ACIDS

BACKGROUND OF THE INVENTION

The recent literature discloses a variety of mercaptoacyl amino acids which are useful for inhibiting the conversion of angiotensin I to angiotensin II in mammals, and are, therefore, useful in the treatment of hypertension.

U.S. Pat. No. 4,105,776, issued Aug. 8, 1978 discloses mercaptoacyl amino acids wherein the amino acid is, inter alia, proline, 4-hydroxyproline and 4-alkylproline.

U.S. Pat. No. 4,154,935, issued May 15, 1979 discloses mercaptoacyl amino acids wherein the amino acid is, inter alia, 4-halogen substituted proline or 4,4-dihalogen substituted proline.

United Kingdom patent application No. 2,027,025, published Feb. 13, 1980, discloses mercaptoacyl amino acids wherein the amino acid is 5-substituted prolines.

United Kingdom patent application No. 2,028,327 published Mar. 5, 1980, discloses mercaptoacyl amino acids wherein the amino acid is, inter alia, proline substituted in the 3- or 4-position with a group having the formula R—S— or R—O— wherein R is alkyl, alkenyl, alkynyl, phenyl, substituted phenyl, phenylalkyl or substituted phenylalkyl.

U.S. Pat. No. 4,168,267, issued Sept. 18, 1979 discloses phosphinylalkanoyl prolines and esters or salts thereof.

Belgian Pat. No. 879,158 discloses 3-[[(3-sulfanoyl4-chlorophenyl)carbonyl]thio]propionyl proline and thiazolidinecarboxylic acid.

The compounds disclosed by the above mentioned references are disclosed as inhibitors of the action of angiotensin converting enzyme in mammals and as useful hypotensive agents.

BRIEF DESCRIPTION OF THE INVENTION

Compounds having the formula

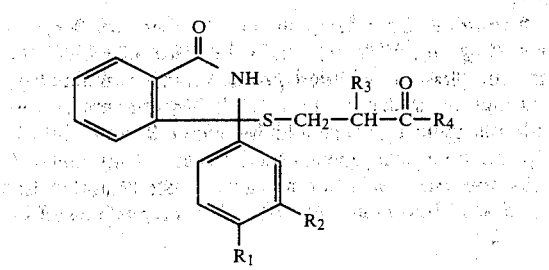

have hypotensive activity. In formula I, and throughout the specification, the symbols are as defined below.

$R_1$ and $R_2$ are the same or different, and each is hydrogen, halogen, trifluoromethyl, or aminosulfonyl ($NH_2SO_2$—);

$R_3$ is hydrogen, alkyl, halogen or trifluoromethyl;

$R_4$ is

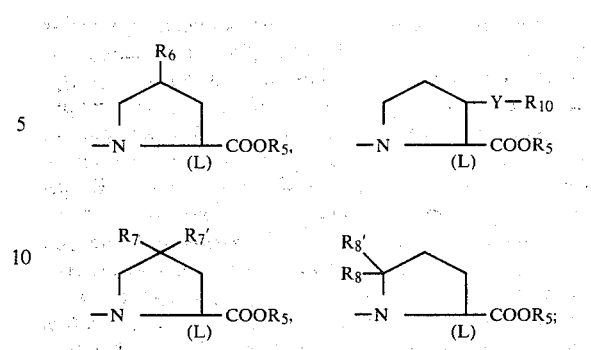

$R_5$ is hydrogen, alkyl, phenylalkyl, or a metal ion;

$R_6$ is hydrogen, hydroxy, alkyl, halogen, azido, amino, cycloalkyl, aryl, arylalkyl, carbamoyloxy $$(-O-\overset{O}{\underset{\|}{C}}-NH_2),$$

N,N-dialkylcarbamoyloxy, or —Y—$R_9$;

$R_7$ and $R_7'$ are the same and each is halogen or —Y—$R_{10}$, or $R_7$ and $R_7'$ together are =O, —O—($CH_2$)$_m$—O— or —S—($CH_2$)$_m$—S—;

$R_8$ is hydrogen and $R_8'$ is phenyl, 2-hydroxyphenyl or 4-hydroxyphenyl or $R_8$ and $R_8'$ together are =O;

$R_9$ is alkyl, aryl, arylalkyl, 1- or 2-naphthyl, or biphenyl;

$R_{10}$ alkyl, aryl or arylalkyl;

Y is oxygen or sulfur; and m is 1 or 2.

The term "aryl", as used throughout the specification either by itself or as part of a larger group, refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl", as used throughout the specification either by itself or as part of a larger group, refers to groups having 1 to 8 carbon atoms. Alkyl groups having 1 to 3 carbon atoms are preferred.

The term "alkoxy", as used throughout the specification either by itself or as part of a larger group, refers to groups having 1 to 8 carbon atoms. Alkoxy groups having 1 to 3 carbon atoms are preferred.

The term "metal ion", as used throughout the specification, refers to mono- and divalent ions such as alkali metals (lithium, sodium, potassium) and alkaline earth metals (calcium, magnesium).

The term "halogen", as used throughout the specification either by itself or as part of a larger group, refers to fluorine, chlorine, bromine and iodine. The preferred halogen groups are fluorine and chlorine.

The term "alkanoyl", as used throughout the specification either by itself or as part of a larger group, refers to groups having 2 to 9 carbon atoms.

DETAILED DESCRIPTION OF THE INVENTION

The compounds of formula I are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I.

Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day, preferably about 1 to 15 mg per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg., preferably about 15 to 200 mg of the diuretic, to a mammalian species in need thereof. Exemplary of the diuretics contemplated for use in combination with a peptide of this invention are the thiazide diuretics, e.g., chlorthiazide, hydrochlorthiazide, flumethiazide, hydroflumethiazide, bendroflumethiazide, methychlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I can be prepared using as reactants a lactam having the formula

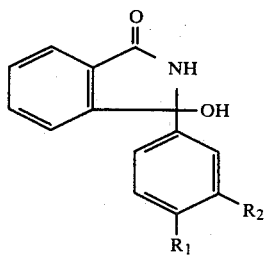

and a mercaptoacylamino acid

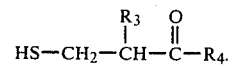

A compound of formula II is first treated with an acid, preferably hydrochloric or hydrobromic acid, and then reacted with an amino acid derivative of formula III.

Lactams of formula II are known; see, for example, U.S. Pat. No. 3,055,904, issued Sept. 25, 1962 which describes those compounds of formula II wherein $R_2$ is aminosulfonyl. Other compounds of formula II are described in Helv. Chim. Acta, 42, 1085 (1959).

Mercaptoacylamino acids of formula III are known. They are obtained by coupling an amino acid having the formula $$H\text{-}R_4 \qquad \qquad IV$$

with an alkanoic acid having the formula

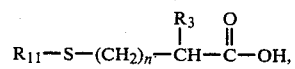

wherein $R_{11}$ is a protecting group, and then deprotecting the sulfhydryl group of the resulting compound. The coupling of an acid of formula V and an amino acid or amino acid ester of formula IV can be accomplished using known amide bond forming procedures that are conventionally used in peptide syntheses. The reaction can be run in the presence of a coupling agent such as dicyclohexylcarbodiimide, or the acid can be activated by formation of its mixed anhydride, symmetrical anhydride, acid halide (preferably acid chloride) or acid ester, or by the use of Woodward reagent K, or N-ethoxycarbonyl-2l-ethoxy-1,2-dihydroquinoline or the like. A review of these methods can be found in *Methoden der Organischen Chemie* (Houben-Weyl), Vol. XV, part II, page 1 et seq. (1974).

The amino acid derivatives of formula IV are known. Various substituted prolines are disclosed by Manger et al., Chem. Rev., 66:47 (1966). Ondetti et al. disclose various alkyl, halogen, ether and thioether substituted prolines in U.S. Pat. Nos. 4,105,776, 4,154,934, and U.K. Application No. 2,028,327. Iwao et al., in U.K. Application No. 2,027,025 disclose various 5-substituted prolines.

As disclosed by Krapcho in U.S. Ser. No. 066,119, filed Aug. 12, 1979, now U.S. Pat. No. 4,217,359, the carbamoyloxy substituted prolines can be obtained by reacting the hydroxy substituted N-protected proline with phosgene and then a dialkylamine. Removal of the N-protecting group yields the desired starting material.

As disclosed by Krapcho in U.S. patent application Ser. No. 99,164, filed Nov. 30, 1979, the prolines of the formula

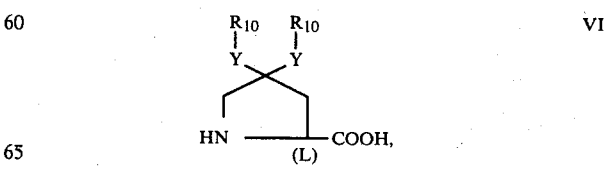

and esters thereof, can be prepared by reacting a keto compound of the formula

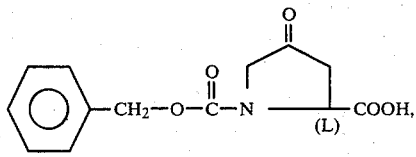

or ester thereof, with an alcohol or thiol having the formula

R₁₀—Y—H    VIII in the presence of an orthoformate or thioformate of the formula HC(Y—R₁₀)₃ and an acid such as concentrated sulfuric acid or p-toluenesulfonic acid. Removal of the carbobenzyloxy group by catalytic hydrogenation when Y is oxygen or by treatment with hydrogen bromide and acetic acid when Y is sulfur yields the desired compound.

As disclosed by Krapcho in U.S. patent application Ser. No. 164,985, filed Aug. 7, 1980, the 4-substituted proline starting materials wherein the substituent $R_6$ is cycloalkyl, aryl, or arylalkyl can be prepared by reacting a 4-keto proline of formula VII, or ester thereof, with a solution of Grignard reagent R₆-Mg-halo    IX or lithium reagent R₆-Li    X to yield the compound of the formula

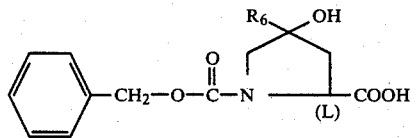

or ester thereof. The compound can be treated with a dehydrating agent such as p-toluenesulfonic acid, sulfuric acid, potassium bisulfate, or trifluoroacetic acid to yield a 3,4-dehydro-4-substituted proline having the formula

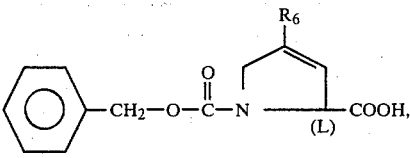

or ester thereof. Removal of the N-benzyloxycarbonyl protecting group and hydrogenation of the resulting compound yields the desired 4-substituted proline derivatives. The substituted proline wherein $R_6$ is cyclohexyl can also be prepared by further hydrogenation of the 4-phenylproline compound.

Preferred compounds of this invention are those compounds of formula I wherein $R_1$ is hydrogen or halogen and $R_2$ is aminosulfonyl.

The following examples are specific embodiments of this invention.

EXAMPLE 1

1-[3-[[1-[3-(Aminosulfonyl)-4-chlorophenyl]2,3-dihydro-3-oxo-1H-isoindol-1yl]thio]-2-methyl-1-oxopropyl]-L-proline A mixture of 1.69 g chlorthalidone, 2.5 g of 1-(3-mercapto-2-methyl-1-oxopropyl)-L-proline and 150 ml ethyl acetate is cooled by an ice bath and then saturated with HCl gas. This mixture is refluxed for one hour. The solvent is evaporated, the residue dissolved in warm saturated sodium bicarbonate solution, and the mixture extracted with ethyl acetate. The aqueous phase is separated and acidified at ice bath temperature. The resulting solid is filtered off, washed with water and dried to yield 1.3 g of the title compound.

Anal. Calc'd for $C_{23}H_{24}ClN_3O_6S_2$: C, 51.34; H, 5.00; N, 7.81; Cl, 6.59; S, 11.92 Found: C, 51.06; H, 4.81; N, 7.12; Cl, 6.37; S, 11.99.

About 1 g of the above material is flash-chromatographed (Whatman LP-1 silica; methylene chloride:methanol:acetic acid=9:0.5:0.5), fractions with $R_f$ 0.29 (silica; methylene chloride; methanol:acetic acid=9.0.5:0.5) are combined, filtered, and evaporated to yield 0.4 g of the title compound as a hemihydrate.

Anal. Calc'd for $C_{23}H_{24}ClN_3O_6S_2 \cdot \frac{1}{2} H_2O$: C, 50.59; H, 4.42; N, 7.69; Cl, 6.48; S, 11.72 Found: C, 50.09; H, 4.56; N, 7.41; Cl, 6.49; S, 11.42.

EXAMPLES 2–40

Following the procedure of Example 1, but substituting the compound listed in column I for 1-(3-mercapto-2-methyl-1-oxopropyl)-L-proline, yields the compound listed in column II.

| | Column I | Column II |
|---|---|---|
| 2. | 4-hydroxy-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4-hydroxy-L-proline |
| 3. | 4-methyl-1-(3-mercapto-2-methyl-1-oxopropyl)-L-proline | 1-[3-[[1-[3-(aminosulfonyl)-4-chlorophenyl]2,3-dihydro-3-oxo-1H-isoindol-1-yl]thio]-2-methyl-1-oxopropyl]-4-methyl-L-proline |
| 4. | 4-fluoro-1-(3-mercapto-2-methyl-1-oxopropyl)-L-proline | 1-[3-[[1-[3-(aminosulfonyl)-4-chlorophenyl]2,3-dihydro-3-oxo-1H-isoindol-1-yl]thio]-2-methyl-1-oxopropyl]-4-fluoro-L-proline |
| 5. | 4-azido-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4-azido-L-proline |
| 6. | 4-amino-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4-amino-L-proline |

-continued

| | Column I | Column II |
|---|---|---|
| 7. | 4-phenyl-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4-phenyl-L-proline |
| 8. | 4-cyclohexyl-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4-cyclohexyl-L-proline |
| 9. | 4-(phenylmethyl)-1-(3-mercapto-2-methyl-1-oxopropyl)-L-proline | 1-[3-[[1-[3-(aminosulfonyl)-4-chlorophenyl]2,3-dihydro-3-oxo-1H-isoindol-1-yl]thio]-2-methyl-1-oxopropyl]-4-(phenylmethyl)-L-proline |
| 10. | 4-(carbamoyloxy)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl] thio]-2-methyl-1-oxopropyl]-4-(carbamoyloxy)-L-proline |
| 11. | 4-(N,N-dimethylcarbamoyloxy)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4-(N,N-dimethylcarbamoyloxy)-L-proline |
| 12. | 4-methoxy-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4-methoxy-L-proline |
| 13. | 4-phenoxy-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4-phenoxy-L-proline |
| 14. | 4-(phenylmethoxy)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4-(phenylmethoxy)-L-proline |
| 15. | 4-(1-naphthyloxy)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4-(1-naphthyloxy)-L-proline |
| 16. | 4-(p-biphenyloxy)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4-(1-biphenyloxy)-L-proline |
| 17. | 4-(methylthio)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4-(methylthio)-L-proline |
| 18. | 4-(phenylthio)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4-(phenylthio)-L-proline |
| 19. | 4-[phenyl(methylthio)]-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl 4-[phenyl(methylthio)]-L-proline |
| 20. | 4-(2-naphthylthio)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]4-(2-naphthylthio)-L-proline |
| 21. | 4-(p-biphenylthio)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4-(p-biphenylthio)-L-proline |
| 22. | 3-methoxy-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-3-methoxy-L-proline |
| 23. | 3-phenoxy-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-3-phenoxy-L-proline |
| 24. | 3-phenylmethoxy-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-3-phenylmethoxy-L-proline |
| 25. | 3-(ethylthio)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-3-(ethylthio)-L-proline |
| 26. | 3-(phenylthio)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-3-(phenylthio)-L-proline |
| 27. | 3-[phenyl(methylthio)]-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl] thio]-2-methyl-1-oxopropyl]-3-[phenyl(methylthio)]-L-proline |
| 28. | 4,4-difluoro-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4,4-difluoro-L-proline |
| 29. | 4,4-dimethoxy-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4,4-dimethoxy-L-proline |
| 30. | 4,4-di(methylthio)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4,4-di(methylthio)-L-proline |
| 31. | 4,4-diphenoxy-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4,4-diphenoxy-L-proline |

-continued

| Column I | Column II |
|---|---|
| 32. 4,4-di(phenylthio)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4,4-di(phenylthio)-L-proline |
| 33. 4,4-di[phenyl(methylthio)]-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4,4-di[phenyl(methylthio)]-L-proline |
| 34. 4-oxo-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4-oxo-L-proline |
| 35. 4,4-(ethylenedioxy)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4,4-(ethylenedioxy)-L-proline |
| 36. 4,4-(propylenedithio)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-4,4-(propylenedithio)-L-proline |
| 37. 5-phenyl-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-5-phenyl-L-proline |
| 38. 5-(2-hydroxyphenyl)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-5-(2-hydroxyphenyl)-L-proline |
| 39. 5-(4-hydroxyphenyl)-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-5-(4-hydroxyphenyl)-L-proline |
| 40. 5-oxo-1-(3-mercapto-2-methyl-1-oxopropyl)-L-proline | 1-[3-[[1-[3-(aminosulfonyl)-4-chlorophenyl]-2,3-dihydro-3-oxo-1H-isoindol-1-yl]thio]-2-methyl-1-oxopropyl]-5-oxo-L-proline |

EXAMPLES 41–43

Following the procedure of Example 1, but substituting the compound listed in column I for chlorthalidone, yields the compound listed in column II.

| Column I | Column II |
|---|---|
| 41. 5-(1-hydroxy-3-oxo-1-isoindolinyl)-benzenesulfonamide | 1-[3-[[1-[3-(aminosulfonyl)phenyl]-2,3-dihydro-3-oxo-1H-isoindol-1-yl]thio]-2-methyl-1-oxopropyl]-L-proline |
| 42. 5-(1-hydroxy-3-oxo-1-isoindolinyl)-2-(trifluoromethyl)benzenesulfonamide | 1-[3-[[1-[3-(aminosulfonyl)-4-(trifluoromethyl)phenyl]-2,3-dihydro-3-oxo-1H-isoindol-1-yl]thio]-2-methyl-1-oxo-propyl]-L-proline |
| 43. 3-hydroxy-3-phenylphthalimidine | 1-[3-[[2,3-dihydro-3-oxo-1H-isoindol-1-yl]thio]-2-methyl-1-oxopropyl]-L-proline |

What is claimed is:
1. A compound having the formula

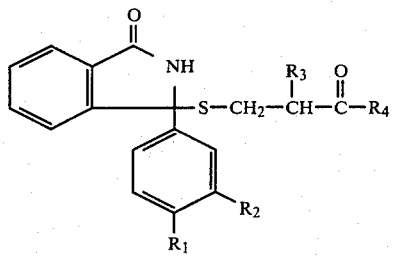

wherein $R_1$ and $R_2$ are the same or different, and each is hydrogen, halogen, trifluoromethyl, or aminosulfonyl;

$R_3$ is hydrogen, alkyl, halogen or trifluoromethyl;

$R_4$ is

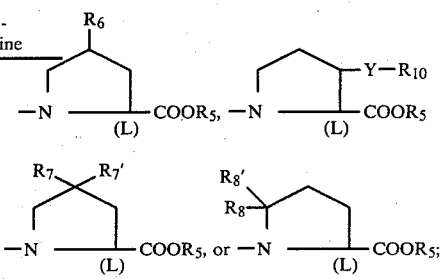

$R_5$ is hydrogen, alkyl, phenylalkyl, or a metal ion;
$R_6$ is hydrogen, hydroxy, alkyl, halogen, azido, amino, cycloalkyl, aryl, arylalkyl, carbamoyloxy, N,N-dialkylcarbamoyloxy, or —Y—$R_9$;
$R_7$ and $R_7'$ are the same and each is halogen or —Y—$R_{10}$, or $R_7$ and $R_7'$ together are =O, —O—$(CH_2)_m$—O— or —S—$(CH_2)_m$—S—;
$R_8$ is hydrogen and $R_8'$ is phenyl, 2-hydroxyphenyl or 4-hydroxyphenyl or $R_8$ and $R_8'$ together are =O;
$R_9$ is alkyl, aryl, arylalkyl, 1- or 2-naphthyl, or biphenyl;
$R_{10}$ is alkyl, aryl or arylalkyl;

Y is oxygen or sulfur; and m is 1 or 2.

2. A compound in accordance with claim 1 wherein $R_1$ is hydrogen or halogen and $R_2$ is aminosulfonyl.

3. A compound in accordance with claim 1 wherein $R_1$ is chloro and $R_2$ is aminosulfonyl.

4. A compound in accordance with claim 1 wherein $R_3$ is methyl.

5. A compound in accordance with claim 1 wherein $R_4$ is

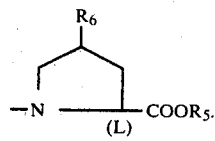

6. A compound in accordance with claim 5 wherein $R_6$ is hydrogen.

7. The compound in accordance with claim 6, 1-[3-[[1-[3-(aminosulfonyl)-4-chlorophenyl]-2,3-dihydro-3-oxo-1H-isoindol-1-yl]thio]-2-methyl-1-oxopropyl]-L-proline.

* * * * *

UNITED STATES PATENT AND TRADEMARK OFFICE
CERTIFICATE OF CORRECTION

PATENT NO. : 4,312,809
DATED : 1/26/82
INVENTOR(S) : Rudiger D. Haugwitz

It is certified that error appears in the above—identified patent and that said Letters Patent is hereby corrected as shown below:

In column 1, line 37, please add a hyphen (-) after sulfanoly]

In column 4, line 37, please delete "]" after ethoxycarbonyl-2.

Signed and Sealed this

Seventh Day of September 1982

[SEAL]

Attest:

Attesting Officer

GERALD J. MOSSINGHOFF
Commissioner of Patents and Trademarks